US008677813B2

(12) United States Patent
Sellars et al.

(10) Patent No.: US 8,677,813 B2
(45) Date of Patent: Mar. 25, 2014

(54) APPARATUS AND A METHOD OF TESTING THE ADHESION STRENGTH AND/OR COHESIVE STRENGTH OF A COATING

(75) Inventors: Christopher Sellars, Derby (GB); Andrew Hewitt, Derby (GB)

(73) Assignee: Rolls-Royce plc, London (GB)

( * ) Notice: Subject to any disclaimer, the term of this patent is extended or adjusted under 35 U.S.C. 154(b) by 606 days.

(21) Appl. No.: 13/024,551

(22) Filed: Feb. 10, 2011

(65) Prior Publication Data
US 2011/0214497 A1 Sep. 8, 2011

(30) Foreign Application Priority Data

Mar. 8, 2010 (GB) .................................. 1003792.7

(51) Int. Cl.
*G01N 19/04* (2006.01)
(52) U.S. Cl.
USPC ........................................................ 73/150 A
(58) Field of Classification Search
USPC ............................................... 73/150 A, 827
See application file for complete search history.

(56) References Cited

U.S. PATENT DOCUMENTS

| 557,868 A | 4/1896 | Packham |
| 4,304,135 A * | 12/1981 | Peterson et al. ................. 73/799 |
| 4,413,510 A | 11/1983 | McCusker et al. |
| 5,144,845 A * | 9/1992 | Pyke ........................... 73/150 A |

FOREIGN PATENT DOCUMENTS

| GB | 1 455 534 | 11/1976 |
| JP | A-1-163641 | 6/1989 |
| JP | A-2002-214123 | 7/2002 |
| SU | 945760 | 7/1982 |
| SU | 1208497 A | 1/1986 |
| SU | 1352325 A1 | 11/1987 |
| SU | 1359724 A1 | 12/1987 |
| SU | 1809370 A1 | 4/1993 |

OTHER PUBLICATIONS

Extended European Search Report issued on Nov. 29, 2012 in European Patent Application 11153862.5.
Cree et al., "Strain-energy method for determining residual stresses in anodised thin films," *Transactions of the Institute of Metal Finishing*, vol. 84, No. 5, pp. 246-251, 2006.
British Search Report issued in British Patent Application No. GB1003792.7 on May 20, 2010.

* cited by examiner

*Primary Examiner* — Peter MacChiarolo
*Assistant Examiner* — Alex Devito
(74) *Attorney, Agent, or Firm* — Oliff PLC

(57) ABSTRACT

An apparatus (10) to test the adhesion strength and/or cohesive strength of a coating (12) comprises a first member (14) having an aperture (16) and a second member (18) locatable in the aperture (16) in the first member (14). A temperature sensor (20) is arranged to measure the temperature of the first member (14). A third member (22) and a fourth member (24) are mounted on the first member (14). The third member (22) has a first strain gauge (26) to measure the strain in a first direction and the fourth member (24) has a second strain gauge (28) to measure the strain in a second direction perpendicular to the first direction. A device (30) is arranged to apply a tensile load to move the second member (18) from a first position where the second member (18) is located in the aperture (16) in the first member (14) and the surfaces (15, 19) of the first and second members (14, 18) are substantially flush to a second position where the surfaces (15, 19) of the first and second members (14, 18) are not flush and a load sensor (32) is arranged to measure the adhesive strength and/or cohesive strength of a coating (12) deposited on the surfaces (15, 19) of the first and second members (14, 18).

22 Claims, 2 Drawing Sheets

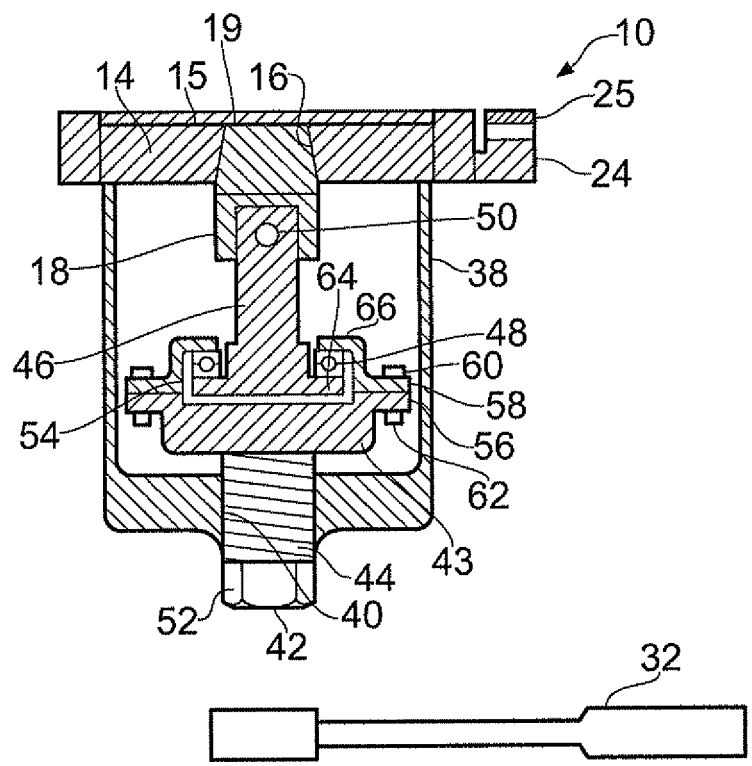
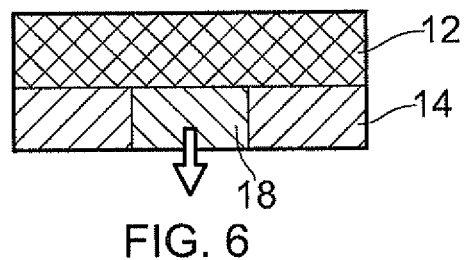
FIG. 5
FIG. 6
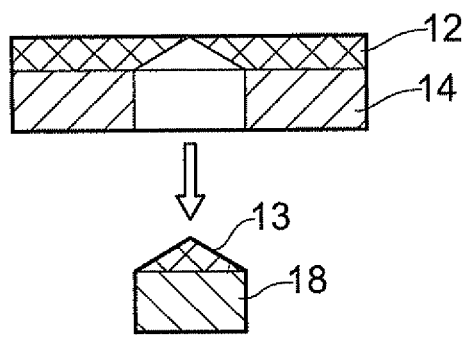
FIG. 7
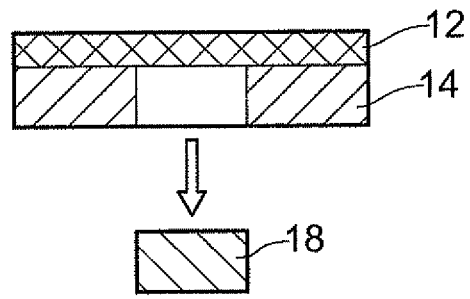
FIG. 8

APPARATUS AND A METHOD OF TESTING THE ADHESION STRENGTH AND/OR COHESIVE STRENGTH OF A COATING

The present invention relates to an apparatus and a method of testing the adhesion strength and/or cohesive strength of a coating, and in particular to an apparatus and a method of testing the adhesion strength and/or cohesive strength of a thermally sprayed coating, for example an abradable coating or a thermal barrier coating.

It is known to test the adhesion strength of a coating by depositing the coating on the surface of a substrate, adhesively bonding a fixture to the opposite surface of the coating and then applying a tensile load to the coating using the substrate and fixture.

A problem with this arrangement is that the test effectively only assesses the adhesion strength between the substrate and the coating if the adhesive strength is less than the cohesive strength of the coating. That is to say a weak coating, e.g. an abradable coating, may fail cohesively prior to fully testing the adhesive strength between the coating and the substrate. Furthermore, if the coating is an abradable coating the adhesive used to adhesively bond the fixture to the coating may diffuse into the abradable coating, provides a degree of reinforcement to the abradable coating and hence contaminates the test results by increasing the strength of the coating. Any test using an adhesive to adhesively bond the coating to a fixture requires a period of time to cure the adhesive. Current adhesive tests do not take into account the residual stress generated in the coating during the deposition of the coating. The residual stress in the coating is a significant factor which determines the toughness, resistance to cracking and/or spallation of a coating.

Accordingly the present invention seeks to provide a novel apparatus to test the adhesion strength or cohesive strength of a coating.

Accordingly the present invention provides an apparatus to test the adhesion strength and/or cohesive strength of a coating comprising a first member having an aperture and a second member locatable in the aperture in the first member, a temperature sensor arranged to measure the temperature of the first member, a first strain gauge to measure the strain in a first direction, a second strain gauge to measure the strain in a second direction perpendicular to the first direction, a device to apply a tensile load to move the second member from a first position where the second member is located in the aperture in the first member and the surfaces of the first and second members are substantially flush to a second position where the surfaces of the first and second members are not flush and a load sensor to measure the adhesive strength and/or cohesive strength of a coating deposited on the surfaces of the first and second members.

Preferably the comprises a third member mounted on the first member and a fourth member mounted on the first member, the third member having the first strain gauge to measure the strain in the first direction, the fourth member having the second strain gauge to measure the strain in the second direction perpendicular to the first direction, Preferably the apparatus comprises a retaining member removably securable to the first member to hold the second member in the aperture in the first member.

Preferably the device to apply a tensile load comprises means to convert rotary motion into unidirectional motion of the second member between the first position and the second position.

Preferably the device to apply a tensile load comprises a support structure removably securable to the first member, the support structure having a threaded aperture, a rotatable drive member having a threaded portion, the threaded portion of the rotatable drive member being rotatably mounted in the threaded aperture in the support structure, the non rotatable drive member being mounted on the rotatable drive member by a thrust bearing, the non rotatable drive member being removably securable to the second member.

Preferably the load sensor comprises a torque wrench arrangable to rotate the rotatable drive member.

Preferably the temperature sensor is a thermocouple.

Preferably there are means to analyse the tensile load, the temperature of the first member, the strain in the first direction, the strain in the second direction and the adhesion strength or cohesive strength of the coating to determine the relationship between the temperature and the adhesion strength and/or cohesive strength of the coating.

The present invention also provides a method of testing the adhesion strength and/or cohesive strength of a coating comprising the steps of:
a) providing a first member having an aperture and a second member locatable in the aperture in the first member,
b) depositing a coating on the surfaces of the first member and second member,
c) measuring the temperature of the first member,
d) measuring the residual stresses in a first direction in the deposited coating,
e) measuring the residual stresses in a second direction perpendicular to the first direction in the deposited coating,
f) applying a tensile load to move the second member from a first position where the second member is located in the aperture in the first member and the surfaces of the first and second members are substantially flush to a second position where the surfaces of the first and second members are not flush, and
g) measuring the tensile load to measure the adhesive strength and/or cohesive strength of a coating deposited on the surfaces of the first and second members.

Preferably step a) comprises providing a third member mounted on the first member and a fourth member mounted on the first member, step b) comprises depositing the coating on the third member and fourth member, step d) comprises measuring the residual stresses in the first direction in the coating deposited on the third member and step e) comprises measuring the residual stresses in the second direction perpendicular to the first direction in the coating deposited on the fourth member.

Preferably the method comprises analysing the tensile load, the temperature of the first member, the strain in the first direction, the strain in the second direction and the adhesion strength or cohesive strength of the coating to determine the relationship between the temperature and the adhesion strength and/or cohesive strength of the coating.

Preferably the method comprises analysing the tensile load, the strain in the first direction and the strain in the second direction and modifying the parameters for deposition of the coating to increase the adhesive strength and/or the cohesive strength of the coating.

Preferably the method comprises subsequently adjusting the parameters for deposition of the coating to increase the adhesion strength and/or the cohesive strength of the coating.

Preferably adjusting the parameters for deposition of the coating comprises adjusting the movement of a deposition gun, the stand off distance between the deposition gun and the first member and/or the amount of cooling of the first member.

Preferably step b) comprises thermally spraying the coating.

Preferably thermally spraying the coating comprises plasma spraying, combustion spraying, HVOF spraying.

Preferably the coating is an abradable coating or a thermal barrier coating.

Preferably the thermal barrier coating comprises zirconia or yttria stabilised zirconia.

Preferably the method comprises the steps of h) heating the coating, first member, second member, third member and fourth member to a predetermined temperature and maintaining at the predetermined temperature for a predetermined time and i) cooling to ambient temperature before steps f) and g).

The present invention will be more fully described with reference to the accompanying drawings, in which:

FIG. 5 is an enlarged cross-sectional view through the portion of the apparatus shown in FIG. 1 during testing of a coating;

FIG. 6 is a schematic cross-sectional view through a portion of the apparatus and a deposited coating;

FIG. 7 is a schematic cross-sectional view through a portion of the apparatus and a deposited coating after testing showing cohesive failure of the coating; and FIG. 8 is a schematic cross-sectional view through a portion of the apparatus and a deposited coating after testing showing adhesive failure of the coating.

Figure 1:
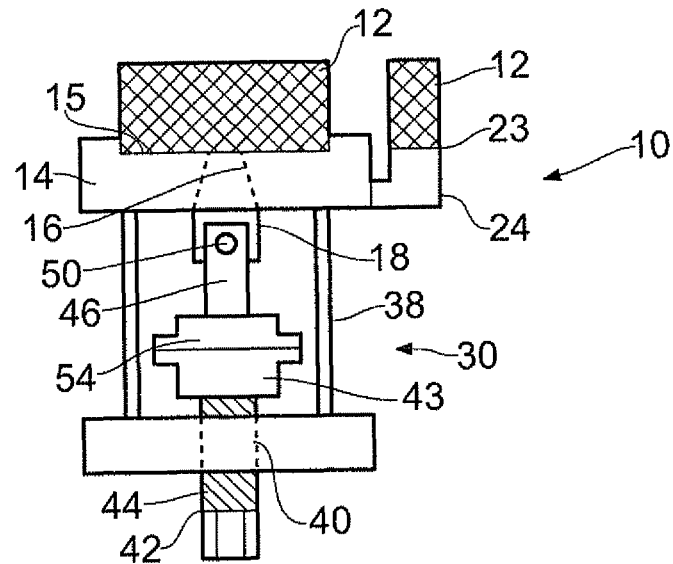
FIG. 1 is a side view of an apparatus to test the adhesion strength and/or cohesive strength of a coating according to the present invention.

An apparatus 10, as shown in FIGS. 1 to 5, to test the adhesion strength and/or cohesive strength of a coating 12 comprises a first member 14 having an aperture 16 and a second member 18 locatable in the aperture 16 in the first member 14. A temperature sensor 20 is arranged to measure the temperature of the first member 14. A third member 22 is mounted on the first member 14 and a fourth member 24 is mounted on the first member 14. The third member 22 has a first strain gauge 26 to measure the strain in a first direction and the fourth member 24 has a second strain gauge 28 to measure the strain in a second direction perpendicular to the first direction. A device 30 is arranged to apply a tensile load to move the second member 18 from a first position where the second member 18 is located in the aperture 16 in the first member 14 and the surfaces 15 and 19 of the first and second members 14 and 18 are substantially flush to a second position where the surfaces 15 and 19 of the first and second members 14 and 18 are not flush and the second member 18 has been pulled out of the aperture 16 in the first member 14. A load sensor 32 is arranged to measure the adhesive strength and/or cohesive strength of a coating 12 deposited on the surfaces 15 and 19 of the first and second members 14 and 18.

Figure 2:
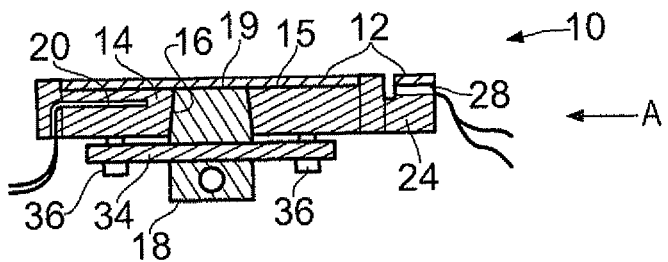
FIG. 2 is an enlarged cross-sectional view through a portion of the apparatus shown in FIG. 1 during deposition of a coating.
Figure 3:
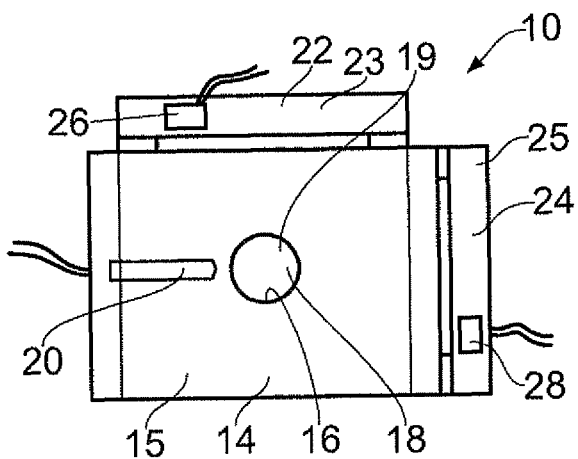
FIG. 3 is a plan view of the portion of the apparatus shown in FIG. 2.
Figure 4:
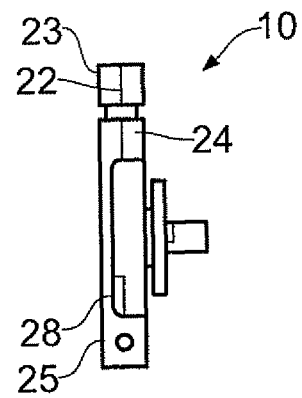
FIG. 4 is a view of the portion of the apparatus shown in FIG. 2 in the direction of arrow A.

The apparatus 10 comprises a retaining member 34, as shown in FIG. 2, which is removably securable to the first member 14 to hold the second member 18 in the aperture 16 in the first member 14. The retaining member 34 is secured onto the first member 14 by screws, or bolts, or other suitable fasteners 36 which pass through apertures in the retaining member 34 and locate in threaded apertures in the first member 14. The retaining member 34 is used to hold the second member 18 in the aperture 14 in the first member 14 during the deposition of the coating 12 onto the flush surfaces 15 and 19 of the first and second members 14 and 18.

The device 30 to apply a tensile load comprises means to convert rotary motion into unidirectional motion of the second member 18 between the first position and the second position. The device 30 to apply a tensile load, as shown in FIGS. 1 and 5, comprises a support structure 38 removably securable to the first member 14 and the support structure 38, a rotatable drive member 42 and a non rotatable drive member 46. The support structure 38 has a threaded aperture 40. The rotatable drive member 42 comprises a main cylindrical member 43, which has a threaded portion 44 extending in a first direction coaxially from the main cylindrical member 43 and the threaded portion 44 of the rotatable drive member 42 is rotatably mounted in the threaded aperture 40 in the support structure 38. The non rotatable drive member 46 is mounted on the rotatable drive member 42 by a thrust bearing 48 and the non rotatable drive member 46 is removably securable to the second member 18 by a pin 50 which locates in a slot. The rotatable drive member 42 also has a square, hexagonal, nut portion 52. The load sensor 32 comprises a torque wrench which is used to rotate the rotatable drive member 42 when placed on the nut portion 52 of the rotatable drive member 42.

The rotatable drive member 42 also has a further hollow cylindrical member 54 which is secured to the main cylindrical member 43 by nuts 60 and bolts, or other suitable fasteners extending through apertures in radially outwardly extending flanges 56 and 58 on the main cylindrical member 43 and the hollow cylindrical member 54 respectively. The hollow cylindrical member 54 has a radially inwardly extending flange 66 at an end remote from the main cylindrical member 43 and the non rotatable drive member 46 is arranged to extend coaxially within the hollow cylindrical member 54. The non rotatable drive member 46 is cylindrical and an end of the non rotatable drive member 46 remote from the second member 18 has a radially outwardly extending flange 64. The thrust bearing 48 is arranged axially between the flanges 64 and 66 on the non rotatable drive member 46 and the hollow cylindrical member 54.

The temperature sensor 20 is a thermocouple or any other suitable temperature sensor. The strain gauges 26, 28 are load cells or any other suitable sensor.

In operation, initially the retaining member 34, as shown in FIG. 2, is secured to the first member 14 to hold the second member 18 in the aperture 16 in the first member 14. Then a coating 12 is deposited onto the surfaces 15 and 19 of the first and second members 14 and 18 respectively and also onto the surfaces 23 and 25 of the third and fourth members 22 and 24 respectively. The coating 12 is deposited onto the above mentioned surfaces 15, 19, 23 and 25 by thermally spraying the coating 12, in particular the coating 12 is deposited by plasma spraying, combustion spraying or HVOF spraying. The coating 12 may be an abradable coating or a thermal barrier coating and the thermal barrier coating may comprise zirconia or yttria stabilised zirconia. The temperature sensor 20 indicates the temperature generated in the first member 14 during the deposition of the coating 12 and the strain gauges 26 and 28 indicate the residual stresses generated in the coating 12 during the deposition of the coating 12.

When the coating 12 and the first and second members 14 and 16 have cooled the retaining member 34 is removed from the first member 14 and the support structure 38 of the device 30 to apply a tensile load is secured to the first member 14, as shown in FIGS. 1 and 5. It is also possible to place the first member 14 and second member 18 in an oven to heat the coating to a predetermined temperature to facilitate ageing of the coating 12 before securing the support structure 38 of the device 30 to the first member 14.

A torque wrench 32 is located on the nut portion 52 of the rotatable drive member 42 and the torque wrench 32 is used to rotate the rotatable drive member 42 and hence move the non rotatable drive member 46 such as to move the second member 18 from a first position where the second member 18 is located in the aperture 16 in the first member 14 and the surfaces 15 and 19 of the first and second members 14 and 18 are substantially flush to a second position where the surfaces 15 and 19 of the first and second members 14 and 18 are not flush and the second member 18 has been pulled out of the aperture 16 in the first member 14. The tensile load required to pull the second member 18 out of the aperture 16 in the first member 14 is indicated by the torque load indicated by the torque wrench 32.

FIG. 6 is a schematic of the coating 12 on the first member 14 and the second member 18 in the as deposited condition before testing of the cohesion strength and/or adhesion strength of the coating 12.

FIG. 7 is a schematic of the coating 12 on the first member 14 and the second member 18 after testing the cohesion strength and/or adhesion strength of the coating 12. In this test it is seen that a portion 13 of the coating 12, the portion of the coating 12 on the surface 19 of the second member 18 has been pulled from the remainder of the coating 12 on the surface 15 of the first member 14. This indicates that the coating 12 has failed due to cohesive failure of the coating 12 and thus the tensile load, e.g. the torque load, indicated by the torque wrench is an indication of the cohesive strength of the coating 12.

FIG. 8 is a schematic of the coating 12 on the first member 14 and the second member 18 after testing the cohesion strength and/or adhesion strength of the coating 12. In this test it is seen that the coating 12 on the surface 19 of the second member 18 has been pulled from the surface 19 of the second member 14, e.g. the coating has delaminated or de-bonded from the second member 18. This indicates that the coating 12 has failed due to adhesive failure of the coating 12 and thus the tensile load, the torque load, indicated by the torque wrench is an indication of the adhesive strength of the coating 12.

For those coatings that do not delaminate from the first member and exhibit complete cohesive failure of the coating, the torque load to failure is used to define the toughness of the coating.

The tensile load to produce failure of the coating 12 is generally higher to produce a cohesive failure than an adhesive failure. The tensile load, the torque load, to produce cohesive failure of the coating is taken as a measure of the toughness of the coating 12.

The tensile load, the temperature of the first member, the strain, the residual stresses, in the first direction, the strain, the residual stresses, in the second direction and the adhesion strength or cohesive strength of the coating may be analysed to determine the relationship between the temperature and the adhesion strength and/or cohesive strength of the coating.

During the deposition of the coating on a component, or article, often the component, or article, is rotated and the gun thermally spraying the coating on to the component, or article, is moved back and forth along the component, or article, parallel to the axis of rotation of the component, or article. Alternatively during deposition of the coating on a component, or article, the component, or article, is held stationary and the gun thermally spraying the coating on to the component, or article, is moved across and along the component. In both these methods of deposition of the coating on the component, or article, the stresses in the coating will be different due to the manner in which the layers of coating are built up on the component, or article, and the type and amount of cooling employed between the layers of the coating. The coating is molten during the deposition process and then the coating solidifies on the component, or article. The solidification of the coating on the component, or article, results in shrinkage of the coating and the shrinkage of the coating produces stresses. The pattern of the spraying used in the deposition of the coating on the component, or article, determines the nature of the stresses in the component, or article. The first and second strain gauges on the third and fourth members are arranged to give an indication of these effects.

The tensile load, the strain, the residual stresses, in the first direction and the strain, the residual stresses, in the second direction may be analysed and then the parameters for deposition of the coating may be modified to increase the adhesive strength and/or the cohesive strength of the coating. The spray sequence and/or the cooling of the component, or article, may be adjusted to adjust the solidification conditions experienced during the deposition of the coating and thus modify the stresses incurred during the deposition of the coating on the component, or article. The spray sequence refers to the movement of the deposition gun relative to the component, or article, or the movement of the component, or article, and the deposition gun. Thus the speed of movement of the deposition gun back and forth along the component and/or the speed of rotation of the component may be adjusted. Alternatively the speed of movement of the deposition gun along and/or the speed of movement of the deposition gun across the component may be adjusted. The stand off distance between the component, or article, and the deposition gun may also be adjusted to control the temperature of the component, or article. The flow rate of a coolant and/or the direction of flow of a coolant may also be adjusted to control the temperature of the component, or article. The coolant may be air, carbon dioxide, nitrogen or an inert gas, e.g. argon. The coolant may be supplied from nozzles mounted on the deposition gun and/or nozzles on the floor or nozzles mounted on other suitable structures.

The speed of movement of the deposition gun and/or component, or article, alters the coating thickness per pass and hence controls the density and hardness of the coating. The stand off distance between the deposition gun and the component, or article, alters the material properties of the coating because the sprayed particles of the coating cool off more before hitting the component, or article, with increasing stand off distance.

The speed of movement of the deposition gun and/or component, or article, the stand off distance between the deposition gun and the component, or article, and the cooling of the component may be controlled to ensure the component, or article, does not overheat during the deposition of the coating.

The present invention allows the stresses in the coating, the temperature, surface temperature, of the component and the structure of the coating to be measured or determined and the relationship and effect of each to be assessed.

The apparatus to test the adhesion strength and/or cohesive strength of a coating according to the present invention is used to establish the best parameters for deposition of a production coating on a component, or article. This would involve depositing a particular coating many times on to the apparatus to test the adhesion strength and/or cohesive strength of a coating according to the present invention using different parameters to determine the best parameters for deposition of the coating onto the component, or article. The apparatus to test the adhesion strength and/or cohesive strength of a coating according to the present invention would then be used in production to assess the quality of the coating deposited on to a component, or article. The component, or article, may be a gas turbine engine component. A thermal barrier coating may be deposited onto a turbine blade, a turbine vane, a turbine shroud, a combustor wall, a combustor tile. An abradable coating may be deposited onto a compressor casing, a fan casing, a turbine casing, a turbine shroud or onto seal structures. Thus, the first, second, third and fourth members and the retaining member are placed in proximity to a component, or components, to be coated such that a coating is deposited onto the first, second, third and fourth members with the same deposition parameters as the coating deposited on the adjacent component, or components. Subsequent testing of the adhesion strength and/or cohesive strength of the coating on the first and second members will indicate the adhesion strength and/or cohesive strength of the coating on the component or components.

Thus, a coating may be deposited onto the apparatus to test the adhesion strength and/or cohesive strength of a coating a number of times under different, adjusted, deposition parameters to determine if the adhesive strength and/or cohesive strength has increased or decreased. If the adhesive strength and/or the cohesive strength has increased the parameters may be used to deposit a coating onto a component, or article.

The advantage of the present invention is that there is no requirement for an adhesive to bond the coating to a testing device and this eliminates the possibility of contamination of the test results by increasing the strength of the coating due to an adhesive. The present invention is able to assess the adhesive strength of the coating without relying on the cohesive strength of the coating. The present invention allows a visual assessment, or qualitative assessment, of the fracture interface and to determine whether the fracture interface is at the bond between the coating and the substrate, and hence an adhesive failure, or within the coating and hence a cohesive failure. The present invention allows a quantitative assessment of the adhesive strength, or cohesive strength, of the coating by measuring the torque load required to provide failure/fracture of the coating. The present invention utilises a small self contained jig, designed for use by an operator without any specialist laboratory support and without any electrical, hydraulic or pneumatic power supplies. The residual stress gauges and the surfaces of the first member and second member are located close together and in the same plane and thus ensure the composition of the coating is consistent, substantially the same, at all these positions.

It may be possible to provide the strain gauges on the first member, rather than provide third and fourth members and position the strain gauges on the third and fourth members.

The inclusion of the strain measurement, residual stress, sensors enables the measurement of the residual strain in the coating for a given set of spray conditions. The strain measurement, residual stress, sensors are able to show a relationship between the residual stress and adhesive shear force. If a relationship can be established between the residual stress and adhesive shear force it is then possible to modify the spraying conditions to reduce residual stress, whilst maintaining cohesive coating stress and therefore improve the service life of a coating on a component.

The invention claimed is:

1. An apparatus to test the adhesion strength and/or cohesive strength of a coating comprises a first member having an aperture and a second member locatable in the aperture in the first member, the first and second members having surfaces, a temperature sensor arranged to measure the temperature of the first member, a first strain gauge to measure the strain in a first direction, a second strain gauge to measure the strain in a second direction perpendicular to the first direction, a device to apply a tensile load to move the second member from a first position where the second member is located in the aperture in the first member and the surfaces of the first and second members are substantially flush to a second position where the surfaces of the first and second members are not flush and a load sensor to measure the adhesive strength and/or cohesive strength of a coating deposited on the surfaces of the first and second members, means to analyse the tensile load, the temperature of the first member, the strain in the first direction, the strain in the second direction and the adhesion strength or cohesive strength of the coating to determine the relationship between the temperature and the adhesion strength and/or cohesive strength of the coating.

2. An apparatus as claimed in claim 1 comprising a third member mounted on the first member and a fourth member mounted on the first member, the third member having the first strain gauge to measure the strain in a first direction, the fourth member having the second strain gauge to measure the strain in a second direction perpendicular to the first direction.

3. An apparatus as claimed in claim 1 comprising a retaining member removably securable to the first member to hold the second member in the aperture in the first member.

4. An apparatus as claimed in claim 1 wherein the device to apply a tensile load comprises means to convert rotary motion into unidirectional motion of the second member between the first position and the second position.

5. An apparatus as claimed in claim 4 wherein the device to apply a tensile load comprises a support structure removably securable to the first member, the support structure having a threaded aperture, a rotatable drive member having a threaded portion, the threaded portion of the rotatable drive member being rotatably mounted in the threaded aperture in the support structure, the non rotatable drive member being mounted on the rotatable drive member by a thrust bearing, the non rotatable drive member being removably securable to the second member.

6. An apparatus as claimed in claim 5 wherein the load sensor comprises a torque wrench arrangable to rotate the rotatable drive member.

7. An apparatus as claimed in claim 1 wherein the temperature sensor is a thermocouple.

8. A method of testing the adhesion strength and/or cohesive strength of a coating comprising the steps of:
   a) providing a first member having an aperture and a second member locatable in the aperture in the first member, the first and second members having surfaces,
   b) depositing a coating on the surfaces of the first member and second member,
   c) measuring the temperature of the first member,
   d) measuring the residual stresses in a first direction in the deposited coating,
   e) measuring the residual stresses in a second direction perpendicular to the first direction in the deposited coating,
   f) applying a tensile load to move the second member from a first position where the second member is located in the aperture in the first member and the surfaces of the first and second members are substantially flush to a second position where the surfaces of the first and second members are not flush,
   g) measuring the tensile load to measure the adhesive strength and/or cohesive strength of a coating deposited on the surfaces of the first and second members, and
   h) analysing the tensile load, the temperature of the first member, the strain in the first direction, the strain in the second direction and the adhesion strength or cohesive strength of the coating to determine the relationship between the temperature and the adhesion strength and/or cohesive strength of the coating.

9. A method as claimed in claim 8 wherein step a) comprises providing a third member mounted on the first member and a fourth member mounted on the first member, step b) comprises depositing the coating on the third member and fourth member, step d) comprises measuring the residual stresses in the first direction in the coating deposited on the third member and step e) comprises measuring the residual stresses in the second direction perpendicular to the first direction in the coating deposited on the fourth member.

10. A method as claimed in claim 8 comprising analysing the tensile load, the strain in the first direction and the strain in the second direction and modifying the parameters for deposition of the coating to increase the adhesive strength and/or the cohesive strength of the coating.

11. A method as claimed in claim 8 comprising subsequently adjusting the parameters for deposition of the coating to increase the adhesion strength and/or the cohesive strength of the coating.

12. A method as claimed in claim 11 wherein adjusting the parameters for deposition of the coating comprises adjusting the movement of a deposition gun, the stand off distance between the deposition gun and the first member and/or the amount of cooling of the first member.

13. A method as claimed in claim 8 wherein step b) comprises thermally spraying the coating.

14. A method as claimed in claim 13 wherein thermally spraying the coating is selected from the group consisting of plasma spraying, combustion spraying and HVOF spraying.

15. A method as claimed in claim 8 wherein the coating is selected from the group consisting of an abradable coating and a thermal barrier coating.

16. A method as claimed in claim 15 wherein the thermal barrier coating is selected from the group consisting of zirconia and yttria stabilised zirconia.

17. A method as claimed in claim 8 wherein the method comprises the steps of i) heating the coating, first member, second member, third member and fourth member to a predetermined temperature and maintaining at the predetermined temperature for a predetermined time and j) cooling to ambient temperature before steps f) and g).

18. An apparatus to test the adhesion strength and/or cohesive strength of a coating comprises a first member having an aperture and a second member locatable in the aperture in the first member, the first and second members having surfaces, a temperature sensor arranged to measure the temperature of the first member, a first strain gauge to measure the strain in a first direction, a second strain gauge to measure the strain in a second direction perpendicular to the first direction, a device to apply a tensile load to move the second member from a first position where the second member is located in the aperture in the first member and the surfaces of the first and second members are substantially flush to a second position where the surfaces of the first and second members are not flush and a load sensor to measure the adhesive strength and/or cohesive strength of a coating deposited on the surfaces of the first and second members.

19. An apparatus as claimed in claim 18 wherein the device to apply a tensile load comprises means to convert rotary motion into unidirectional motion of the second member between the first position and the second position.

20. An apparatus as claimed in claim 19 wherein the device to apply a tensile load comprises a support structure removably securable to the first member, the support structure having a threaded aperture, a rotatable drive member having a threaded portion, the threaded portion of the rotatable drive member being rotatably mounted in the threaded aperture in the support structure, the non rotatable drive member being mounted on the rotatable drive member by a thrust bearing, the non rotatable drive member being removably securable to the second member.

21. An apparatus as claimed in claim 18 wherein the load sensor comprises a torque wrench arrangable to rotate the rotatable drive member.

22. A method of testing the adhesion strength and/or cohesive strength of a coating comprising the steps of:
  a) providing a first member having an aperture and a second member locatable in the aperture in the first member, the first and second members having surfaces,
  b) depositing a coating on the surfaces of the first member and second member,
  c) measuring the temperature of the first member,
  d) measuring the residual stresses in a first direction in the deposited coating,
  e) measuring the residual stresses in a second direction perpendicular to the first direction in the deposited coating,
  f) applying a tensile load to move the second member from a first position where the second member is located in the aperture in the first member and the surfaces of the first and second members are substantially flush to a second position where the surfaces of the first and second members are not flush, and
  g) measuring the tensile load to measure the adhesive strength and/or cohesive strength of a coating deposited on the surfaces of the first and second members.

* * * * *